US00PP15085P2

(12) United States Plant Patent
Oliver

(10) Patent No.: US PP15,085 P2
(45) Date of Patent: Aug. 17, 2004

(54) HEUCHERA PLANT NAMED 'FROSTED VIOLET'

(50) Latin Name: ***Heuchera* sp.**
Varietal Denomination: Frosted Violet

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 5 days.

(21) Appl. No.: 10/324,935

(22) Filed: Dec. 20, 2002

(51) Int. Cl.[7] ..... A01H 5/00
(52) U.S. Cl. ..... Plt./263

(58) Field of Search ..... Plt./263

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of Heuchera plant named 'Frosted Violet', characterized by its full, densely foliated and uniformly mounded plant habit; upper surfaces of leaves silvery purple in color; lower leaf surfaces dark purple in color; numerous showy pink-colored flowers arranged on erect to outwardly spreading panicles; long flowering period extending from early to late summer; and excellent garden performance.

3 Drawing Sheets

Botanical classification/cultivar designation: Heuchera sp. cultivar Frosted Violet.

BACKGROUND OF THE INVENTION

The present invention relates to a new and distinct cultivar of Heuchera plant, botanically known as Heuchera sp. and hereinafter referred to by the name 'Frosted Violet'.

The new Heuchera is a product of a planned breeding program conducted by the Inventor in Scottdale, Pa. The objective of the breeding program is to create new Heuchera cultivars having good plant vigor, dense and uniform plant habit, and showy and attractive flower and leaf coloration.

The new Heuchera was discovered by the Inventor in a controlled environment in Scottdale, Pa., from seedling progeny from a cross-pollination made by the Inventor in May, 1998, of the Heuchera cultivar Silver Lode, disclosed in U.S. Plant Pat. No. 13,339, as the female, or seed, parent with the Heuchera cultivar Bronze Wave, not patented, as the male, or pollen, parent. The new Heuchera was selected by the Inventor in May, 1999. The selection of this plant was based on its desirable flower and foliage coloration.

Asexual reproduction of the new Heuchera by cuttings taken in a controlled environment in Scottdale, Pa., since August, 1999, has shown that the unique features of this new Heuchera are stable and reproduced true to type in successive generations.

SUMMARY OF THE INVENTION

The cultivar Frosted Violet has not been observed under all possible environmental conditions. The phenotype may vary somewhat with variations in environment such as temperature and light intensity, without, however, any variance in genotype.

The following traits have been repeatedly observed and are determined to be the unique characteristics of 'Frosted Violet'. These characteristics in combination distinguish 'Frosted Violet' as a new and distinct cultivar of Heuchera:

1. Full, densely foliated and uniformly mounded plant habit.

2. Upper surfaces of leaves silvery purple in color; lower leaf surfaces dark purple in color.
3. Numerous showy pink-colored flowers arranged on erect to outwardly spreading panicles.
4. Long flowering period extending from early to late summer.
5. Excellent garden performance.

Plants of the new Heuchera can be compared to plants of the female parent, the cultivar Silver Lode. In side-by-side comparisons conducted by the Inventor in Scottdale, Pa., plants of the new Heuchera differed from plants of the cultivar Silver Lode in the following characteristics:

1. Leaves of plants of the new Heuchera were more sharply lobed than leaves of plants of the cultivar Silver Lode.
2. Leaves of plants of the new Heuchera had silvery purple-colored upper surfaces whereas leaves of plants of the cultivar Silver Lode had silvered bronze-colored upper surfaces.
3. Leaf petioles of plants of the new Heuchera were pubescent whereas leaf petioles of plants of the cultivar Silver Lode were glabrous.
4. Inflorescences of plants of the new Heuchera were more outwardly spreading than inflorescences of plants of the cultivar Silver Lode.
5. Flowers of plants of the new Heuchera were pink in color whereas flowers of plants of the cultivar Silver Lode were greenish white in color.

Plants of the new Heuchera can be compared to plants of the male parent, the cultivar Bronze Wave. In side-by-side comparisons conducted by the Inventor in Scottdale, Pa., plants of the new Heuchera differed from plants of the cultivar Bronze Wave in the following characteristics:

1. Leaves of plants of the new Heuchera were smaller than leaves of plants of the cultivar Bronze Wave.
2. Leaves of plants of the new Heuchera had silvery purple-colored upper surfaces whereas leaves of plants of the cultivar Bronze Wave had bronze green-colored upper surfaces.

3. Plants of the new Heuchera flowered about three to four weeks earlier than plants of the cultivar Bronze Wave.
4. Inflorescences of plants of the new Heuchera were longer than inflorescences of plants of the cultivar Bronze Wave.
5. Flowers of plants of the new Heuchera were pink in color whereas flowers of plants of the cultivar Bronze Wave were greenish white in color.

Plants of the new Heuchera can be compared to plants of the cultivar Silver Scrolls, disclosed in U.S. Plant Pat. No. 12,066. In side-by-side comparisons conducted by the Inventor in Scottdale, Pa., plants of the new Heuchera differed from plants of the cultivar Silver Scrolls in the following characteristics:

1. Leaves of plants of the new Heuchera were more sharply lobed than leaves of plants of the cultivar Silver Scrolls.
2. Leaves of plants of the new Heuchera had silvery purple-colored upper surfaces whereas leaves of plants of the cultivar Silver Scrolls had silvery red purple-colored upper surfaces.
3. Leaf petioles of plants of the new Heuchera were pubescent whereas leaf petioles of plants of the cultivar Silver Scrolls were glabrous.
4. Inflorescences of plants of the new Heuchera were more outwardly spreading than inflorescences of plants of the cultivar Silver Scrolls.
5. Flowers of plants of the new Heuchera were smaller and darker pink in color than flowers of plants of the cultivar Silver Scrolls.

Plants of the new Heuchera can also be compared to plants of the cultivar Regina, not patented. In side-by-side comparisons conducted by the Inventor in Scottdale, Pa., plants of the new Heuchera differed from plants of the cultivar Regina in the following characteristics:

1. Leaves of plants of the new Heuchera were more sharply lobed than leaves of plants of the cultivar Regina.
2. Leaves of plants of the new Heuchera had silvery purple-colored upper surfaces whereas leaves of plants of the cultivar Regina had grayed green-colored upper surfaces.
3. Leaf petioles of plants of the new Heuchera were more densely pubescent than leaf petioles of plants of the cultivar Regina.
4. Inflorescences of plants of the new Heuchera were taller than inflorescences of plants of the cultivar Regina.
5. Flowers of plants of the new Heuchera were smaller than flowers of plants of the cultivar Regina.

BRIEF DESCRIPTION OF THE PHOTOGRAPHS

The accompanying colored photographs illustrate the overall appearance of the new Heuchera, showing the colors as true as it is reasonably possible to obtain in colored reproductions of this type. Colors in the photographs may differ slightly from the color values cited in the detailed botanical description which accurately describe the colors of the new Heuchera.

The photograph on the first sheet comprises a side perspective view of a typical one-year old flowering plant of 'Frosted Violet'.

The photograph on the second sheet is a close-up view of the leaves of a typical plant of 'Frosted Violet'.

The photograph on the third sheet is a close-up view of a typical inflorescence of 'Frosted Violet'.

DETAILED BOTANICAL DESCRIPTION

In the following description, color references are made to The Royal Horticultural Society Colour Chart, 1995 Edition, except where general terms of ordinary dictionary significance are used. The following detailed botanical description describes plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: Heuchera sp. cultivar Frosted Violet.

Parentage:

*Female, or seed, parent.*—Heuchera sp. cultivar Silver Lode, disclosed in U.S. Plant Pat. No. 13,339.

*Male, or pollen, parent.*—Heuchera sp. cultivar Bronze Wave, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright to outwardly spreading panicles with pink-colored flowers. Vigorous and robust growth habit.

*Plant size.*—Height, soil level to top of foliar plane: About 20 cm. Height, soil level to top of panicles: About 90 cm. Diameter or spread: About 40 to 50 cm.

*Foliage description.*—Arrangement: Basal rosette, simple. Length: About 9 cm. Width: About 9 cm. Shape: Cordate; seven-lobed, lobes acute. Apex: Acute. Base: Auriculate to cordate. Margin: Crenate with fine ciliation. Texture, upper and lower surfaces: Slightly pubescent; slightly rough. Venation pattern: Palmate, reticulate. Color: Developing leaves, upper surface: 186A. Developing leaves, lower surface: 187A. Fully expanded leaves, upper surface: 156B underlain with 187A, becoming closer to 198B with development. Fully expanded leaves, lower surface: 187A. Venation, upper surface: 183B, becoming closer to 189A with development. Venation, lower surface: 187A. Petiole: Length: About 20 cm. Diameter: About 2 mm. Texture, upper and lower surfaces: Pubescent. Color, upper and lower surfaces: 59B.

Flower description:

*Appearance/arrangement.*—Single campanulate flowers arranged on numerous erect to outwardly spreading panicles; about 240 flowers and flower buds per flowering stem. Flowers face outward to slightly upright. Flowering continuous. Flowers persistent.

Flowers not fragrant. Time of flowering: Long flowering period, plants flower from June to August in Scottdale, Pa.

*Inflorescence longevity.*—Individual inflorescences last about one week on the plant.

*Inflorescence size.*—Length: About 80 cm. Diameter: About 8 cm.

*Flower size.*—Diameter: About 2.2 mm. Depth (height): About 4.5 mm.

*Flower buds.*—Height: About 1.5 mm. Diameter: About 1 mm. Shape: Globular. Color, at stage of showing color: 59A.

*Sepals.*—Quantity/arrangement: Five sepals; radially symmetrical and fused at base. Calyx length: About 4 mm. Calyx diameter: About 2.2 mm. Shape: Elongate. Apex: Obtuse. Margin: Entire. Texture, upper and lower surfaces: Pubescent. Color, when opening and fully opened, upper and lower surfaces: 66B.

*Petals.*—Quantity/arrangement: Five minute petals; radially symmetrical. Length: About 3.5 mm. Width: About 0.2 mm. Shape: Strap-like to narrowly spatulate. Apex: Obtuse. Margin: Entire. Texture, upper and lower surfaces: Smooth, glabrous. Color, when opening and fully opened, upper and lower surfaces: Close to 155D.

*Flower bracts.*—Length: About 2.5 mm. Width: About 0.5 mm. Shape: Lanceolate. Apex: Acute. Margin: Entire with ciliation. Texture, upper and lower surfaces: Smooth. Color, upper and lower surfaces: 59A.

*Peduncle.*—Strength: Strong. Aspect: Upright to angled outwardly to 30° from vertical. Length: About 41 cm. Diameter: About 2.5 mm. Texture: Smooth. Color: 59A.

*Pedicels.*—Strength: Strong. Aspect: About 45° from vertical. Length: About 1.5 mm. Diameter: About 0.1 mm. Texture: Pubescent. Color: 59B.

*Reproductive organs.*—Androecium: Stamen number: Five per flower. Anther shape: Bi-lobed. Anther size: About 0.2 mm by 0.3 mm. Anther color: 13B. Amount of pollen: Moderate. Pollen color: 13B. Gynoecium: Pistil number: Two per flower. Pistil length: About 4.5 mm. Stigma shape: Round. Stigma color: 62D. Style length: About 3 mm. Style color: 62D. Ovary color: 62D.

*Seed.*—Size: About 0.3 mm by 0.6 mm. Color: Close to 202A.

Disease/pest resistance: Resistance to pathogens and pests common to Heuchera has not been observed on plants grown under commercial conditions.

Weather/temperature tolerance: Plants of the new Heuchera have been observed to have excellent garden performance. Plants of the new Heuchera have demonstrated good tolerance to rain, wind, night temperatures as low as −35° C., and day temperatures as high as 45° C.

It is claimed:

1. A new and distinct cultivar of Heuchera plant named 'Frosted Violet', as illustrated and described.

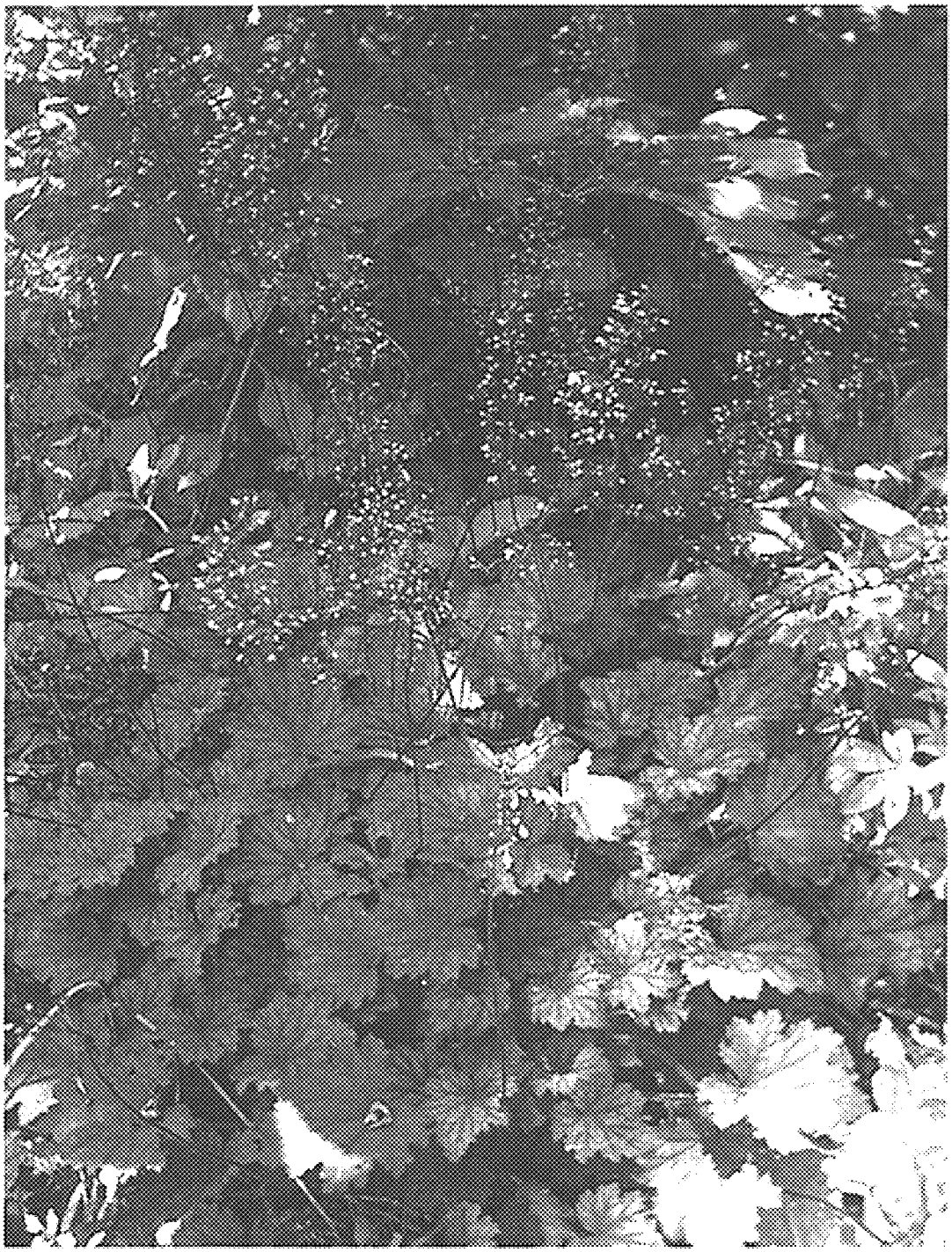

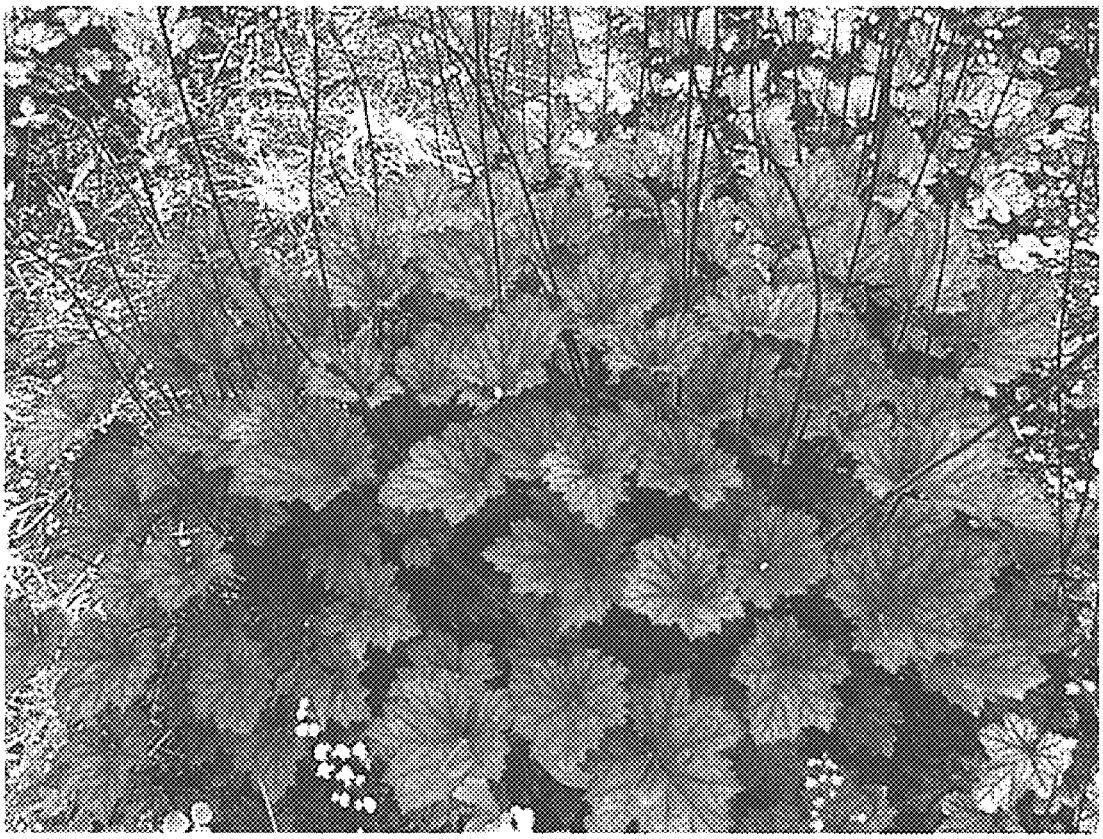

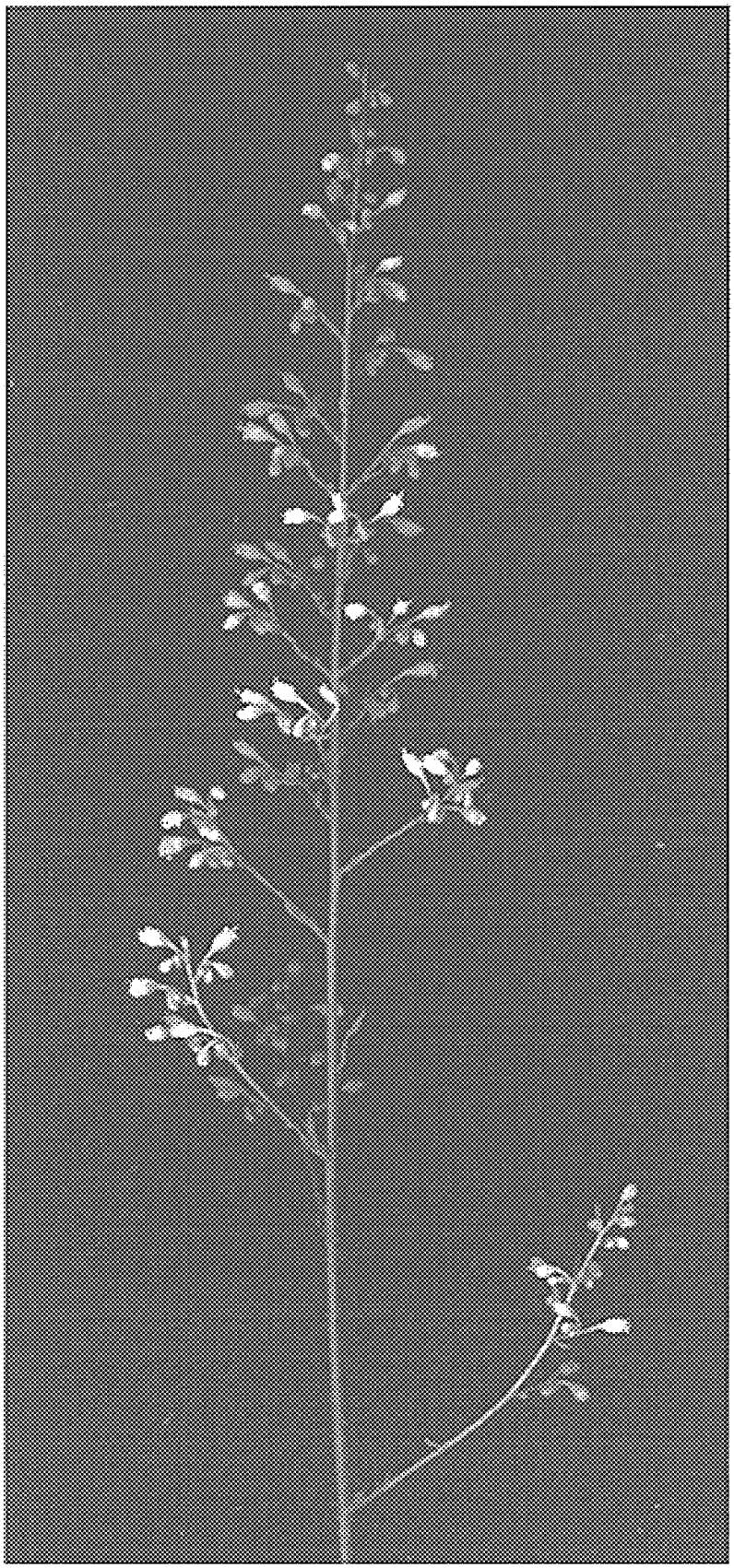

* * * * *